United States Patent [19]
Parsons, Jr. et al.

[11] 4,092,479
[45] May 30, 1978

[54] LABELED 5,5-DIPHENYLHYDANTOIN DERIVATIVES FOR RADIOIMMUNOASSAY

[75] Inventors: George H. Parsons, Jr., Arlington; Thomas Eller, Boston, both of Mass.

[73] Assignee: Baxter Travenol Laboratories, Inc., Deerfield, Ill.

[21] Appl. No.: 673,853

[22] Filed: Apr. 5, 1976

[51] Int. Cl.² .............................................. C07D 233/72
[52] U.S. Cl. ............................. 548/312; 260/112.5 R; 548/309; 424/1.5
[58] Field of Search ................. 260/112.5 R; 548/309, 548/312

[56] References Cited
PUBLICATIONS

Cook, et al. in Research Communication in (1973), Chemical Pathology and Pharmacology, 5, pp. 767–774.

Primary Examiner—Delbert R. Phillips

[57] ABSTRACT

Derivatives of 5,5-diphenylhydantoin having the following structural formula:

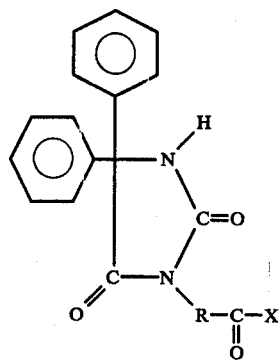

where R is 2-acetyl, 3-propionyl, 4-butyryl or 5-valeryl and X is an unlabeled or radioiodinated amino radical; e.g., (tyrosine, histidine, tyrosinol, histamine). A preferred compound is radioiodinated 5,5-diphenyl-3-(5-valeryl-N-tyrosine) hydantoin. The iodine isotope may be iodine-125 or iodine-131.

1 Claim, No Drawings

LABELED 5,5-DIPHENYLHYDANTOIN DERIVATIVES FOR RADIOIMMUNOASSAY

This invention relates to the radioimmunoassay of the anti-epileptic drug, 5,5-diphenylhydantoin and pertains more specifically to new chemical compounds which are derivatives of 5,5-diphenylhydantoin and which, in radioiodinated form, can be used as tracers, and to the method of making them.

Cook et al. in Research Communications in Chemical Pathology and Pharmacology, Vol. 5, No. 3, p. 767 (1973) have reported the use of 5,5-phenylhydantoin-3-(5-valeric acid) conjugated to bovine serum albumin as an antigen to elicit an antibody response in rabbits for the radioimmunoassay of 5,5-diphenyl-hydantoin. However, the tracer used was 5,5-bis-(phenyl-4-³H)-hydantoin necessitating scintillation counting of the tritium isotope, which is less convenient than gamma counting of iodine isotopes. Tritium labeled tracers also generally have a lower specific activity than iodinated tracers, which may limit the sensitivity of the radioimmunoassay.

An object of this invention is to provide new derivatives of 5,5-diphenylhydantoin which are useful in the preparation of tracer compounds for the radioimmunoassay of 5,5-diphenylhydantoin as well as to provide the tracer compounds themselves. This is accomplished by making derivatives with the following structural formula:

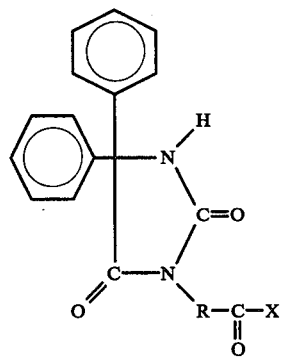

In the foregoing structural formula,

is a straight or branched chain aliphatic acyl group in which R contains from 1 to 7 carbon atoms and in which R may contain, in addition to carbon and hydrogen, up to two hydroxyl and amino groups. Among the acyl groups included are 2-acetyl, 3-propionyl, 4-(2-hydroxybutyryl), 4-(3-hydroxybutyryl), 3-(2-methylpropionyl), 5-valeryl, 4-isovaleryl, 4-(3-aminoisovaleryl), 4-(2-hydroxyisovaleryl), 6-caproyl, 6-(2-aminocaproyl), 7-enanthyl, 8-caprylyl, 6-(2-ethylcaproyl), 8-(2-hydroxycaprylyl); of these, 5-valeryl is preferred.

The moiety identified as X in the foregoing structural formula is selected from the group consisting of the following ring-containing amino radicals:

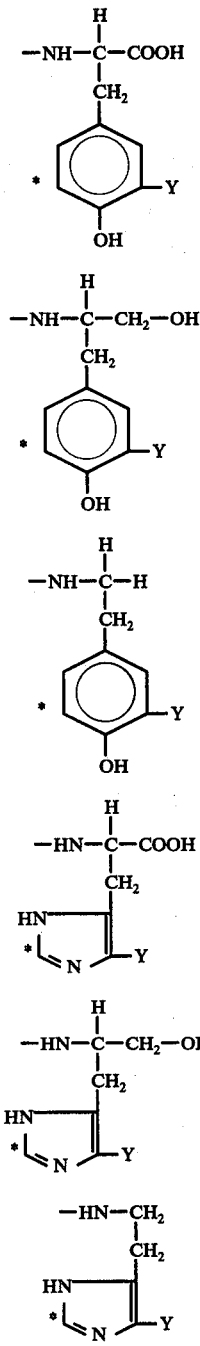

in which Y is hydrogen, fluoro, or lower alkyl (up to 7 carbon atoms), preferably methyl; and amino-terminated polypeptide radicals containing one or more of the aforesaid ring-containing radicals. The ring-containing radicals may be unlabeled or radio-labeled, preferably radioiodinated with one radioiodine atom with the probable positions of labeling indicated by an asterisk. When Y is hydrogen, the ring-containing radicals may be radioiodinated with two radioiodine atoms, one being in the Y position, but this is not preferred. The radioiodine is generally $^{125}I$, but other iodine isotopes such as $^{131}I$ may also be used. Radiolabeling is preferably carried out after coupling of the ring-containing radical is complete.

These compounds are prepared from the 3-sodium salt of 5,5-diphenylhydantoin, which is reacted with the ω-halogenated lower alkyl ester of the desired carboxylic acid to produce 5,5-diphenylhydantoin-3-(ω-carboxylic acid ester). The ester is then converted to the corresponding acid by hydrolysis. The 5,5-diphenylhydantoin-3-(ω-carboxylic acid) is then coupled to the desired ring-containing amino compound via carbodiimide, or ethyl chloroformate activation of the carboxyl group. The resulting compound is then iodinated, preferably by the chloramine T method.

The precursors of compounds of the present invention are prepared by first reacting the sodium salt of 5,5-diphenylhydantoin with ω-halogenated carboxylic acid lower alkyl ester in an inert solvent as described by Cook et al. White Cook et al. employed methyl 5-bromovalerate as the ω-halogenated carboxylic acid lower alkyl ester, other lower alkyl esters of ω-halo aliphatic carboxylic acids having the structure

in which R is defined as above may also be used to provide the desired aliphatic acyl group. ω-Bromocarboxylic acid lower alkyl esters are the preferred halo-derivatives, but chloro- and iodo-derivatives may also be employed. The alkyl portion of the ester may contain one to seven carbon atoms or even more although the methyl and ethyl esters are preferred. The 5,5-diphenylhydantoin-3-(ω-carboxylic acid ester) is then hydrolyzed as described by Cook et al. to form the corresponding free acid.

The 5,5-diphenylhydantoin-3-(ω-carboxylic acid) is then coupled to the desired ring-containing amino compound using either ethyl chloroformate, isobutyl chloroformate or pivaloyl chloride to generate mixed anhydrides. This reaction is carried out in any conventional aprotic solvent at low temperature (0°–10° C.) under anhydrous conditions. Dioxane is the preferred solvent and one equivalent of organic base such as triethylamine, etc., is added to consume hydrochloric acid generated in the mixed anhydride formation. The ring-containing amino compound to be coupled to the mixed anhydride is added to the reaction mixture in either aqueous solution, or in a mixed organic solvent; the reaction of the amino compound with the anhydride is apparently more rapid than hydrolysis of the anhydride.

Isolation of the desired compound is accomplished by addition of the reaction mixture to acidified water. The precipitate obtained can be recrystallized from ethanol. Further purification may be accomplished by preparative thin layer chromatography, gel filtration, affinity chromatography, or other suitable procedures.

The radioiodinated derivatives may be prepared by any one of the following methods:
(1) Chloramine T Method of Hunter-Greenwood, W. Hunter, R. C. Greenwood, Nature, 194, 495 (1962);
(2) Iodine Monochloride Method, M. Ceska, F. Grossmuller, U. Lundkvist, Acta Endcrinologia, 64, 111–125 (1970);
(3) Isotopic Exchange Method, R. E. Counsell, V. V. Ranade, P. Pocha, R. E. Willette, W. Diguilio, J. Pharmaceut. Sciences, 57, 1657 (1968);
(4) Electrolytic Iodination, R. Pennisi, U. Rosa, J. Nuclear Biol. and Medicine, 13, 64 (1964); and
(5) Enzymatic Iodination, H. Van Vanakis, J. J. Langone, L. J. Riceberg, L. Levine, Cancer Research 34, 2546–2552 (1974).

The marginally water soluble products of this invention may be iodinated in inert solvents such as water or water-alcohol mixtures.

Separation of unreacted radioactive iodine is accomplished by gel filtration and the use of aqueous solvents that elute selectively unreacted inorganic iodide and the desired iodinated product.

EXAMPLE 1

A. A mixture of 1.1 gm of 3-sodium 5,5-diphenylhydantoin and 0.8 gm of methyl 5-bromovalerate in 20 ml of dimethylformamide is heated with stirring to 60° C. for 3 hours. The reaction mixture is added to 300 ml of 30% saturated ammonium sulfate and allowed to crystallize for 72 hours to yield crude 5,5-diphenylhydantoin 3-(5-valeric acid methyl ester), m.p. 84°–90° C. On recrystallization from methanol 0.67 gm of a white crystalline material is obtained, m.p. 94°–96° C.

B. The ester obtained in 1-A was hydrolyzed by refluxing for 3 hours in 0.5 normal hydrochloric acid in 10% aqueous dioxane. The desired acid crystallized on standing at 4° C. for 18 hours. The crude acid had a m.p. of 135°–145° C. which was raised to 161°–163° C. on recrystallization from ethyl acetate. A yield of 280 mg of the pure acid was obtained starting with 0.67 gm of ester.

C. Fifteen mg of 5,5-diphenylhydantoin 3-(5-valeric acid) was added to 250 microl. of dioxane in a 12 × 75 mm glass test tube. The acid went into solution on the addition of 50 microl. of 10% triethylamine in dioxane. After chilling to about 10° C in an ice water bath, 50 microl. of 10% ethyl chloroformate in dioxane was added and allowed to react for 30 minutes at 10° C. to form the mixed anhydride.

L-Tyrosine, 25.1 mg, was dissolved in 0.5 ml distilled water to which 5 drops of triethylamine had been added. The aqueous L-Tyrosine was added to the cold mixed anhydride solution and allowed to react for 2 hours while the reaction mixture slowly came to room temperature. The entire reaction mixture was added to 5 ml of distilled water acidified with 5 drops of concentrated sulfuric acid and allowed to precipitate for 18 hours at 4° C.

The precipitate was collected by vacuum filtration and recrystallized from ethanol yielding 3 mg of product: 5,5-diphenylhydantoin-3-(5-valeryl-N-tyrosine).

Analogous products of the present invention can be made by substituting other ω-halocarboxylic acid lower alkyl esters for methyl 5-bromovalerate and by substituting, in place of tyrosine, other ring-containing amino compounds such as tyrosinol, 4-(2-aminoethyl) phenol, histidine, histidinol, histamine, or aminoterminated polypeptide containing one or more of the X radicals as defined above.

EXAMPLE 2

Radioiodination of 5,5-diphenylhydantoin-3-(5-valeryl-N-tyrosine) was effected by the method of Hunter and Greenwood. 10 microl. of a solution (1 mg in 7.0 ml of ethanol) of 5,5-diphenylhydantoin-3-(5-valeryl-N-tyrosine) was diluted in a clean 12 × 75 mm glass test tube with 120 microl. of 0.5 molar phosphate buffer, pH 7.4. To this mixture was added lmCi of sodium iodide $^{125}$I in 20 microl. of 0.1 normal NaOH, followed by 20 microl. of an aqueous solution of chloramine T (70 mg in 10 ml of distilled water).

After reaction at room temperature for 2 minutes with occasional shaking the reaction was quenched by the addition of 40 microl. of a solution of sodium metabisulfite (70 mg in 10 ml of distilled water). The reaction mixture was transferred with a Pasteur pipet to a 1 × 10 cm Sephadex G-10 column that had previously been equilibrated with a 0.1 molar phosphate buffer, pH 8.5. The equilibration buffer was used to elute unreacted sodium iodide. Five ml fractions were collected.

About one-third of the radioactivity was eluted in the phosphate buffer. The remaining activity was retained on the column until the eluting buffer was changed to distilled water. Four 5 ml water fractions were collected; these contained about two-thirds of the radioactivity initially put on the column and represented the desired products: 5,5-diphenylhydantoin-3-(5-valeryl-N-3-$^{125}$I tyrosine) and 5,5-diphenylhydantoin-3-(5-valeryl-N-(3,5-$^{125}$I) tyrosine).

The radioiodinated derivatives of the present invention may be used as the labeled antigen in the radioimmunological assay of 5,5-diphenylhydantoin. A radioimmunological procedure which may be used is a modification of the one employed by R. E.. Tigelaar, R. L. Rapport II, J. K. Inman and H. J. Kupferberg, Clinica Chimica Acta 43, 231–241 (1973) for carbon-14 labeled 5,5-diphenylhydantoin.

To 1 ml of pH 7.4 0.01 molar tris buffer which is isotonic in saline and contains 0.1% bacitracin is added 50 microl. of serum, which had been diluted 1 to 100 in distilled water in a 12 × 75 mm glass test tube. About 40 picograms of the radioiodinated derivative described herein, containing about 30,000 counts per minute is added as well as sufficient 5,5-diphenylhydantoin rabbit antibody to produce 30 to 60 percent binding in the absence of unlabeled drug.

The mixture is incubated for one hour at 25° C. Competition for a limited number of antibody binding sites by the labeled compound and the drug determines the amount of antibody-bound tracer at equilibrium. Separation of bound and free radioiodinated compound is achieved by the dextran-coated charcoal method of Herbert et al. J. Clin. Endocr. 25, 1375–1384 (1965), resulting in selective removal of free labeled and unlabeled compound by the charcoal, which is then separated by centrifugation and decanting. The supernatant containing the antibody bound labeled and unlabeled drug is counted in a gamma counter.

The radioiodinated derivatives of the present invention, unlike the $^{14}$C and $^{3}$H tracers employed by Tigelaar et al. and Cook et al. respectively, may be used with a plastic tube which has been coated with a specific antibody to 5,5-diphenylhydantoin in a procedure similar to that described by Catt et al., Science 158, 1570 (1967).

Patient serum to be assayed is diluted 1 part to 100 parts of distilled water. An aliquot of 50 microl. of the diluted serum is introduced into the bottom of the antibody coated tube. One ml of a pH 7.4 buffer containing 0.01 molar tris, 0.15 molar NaCl, 0.1% bacitracin and 30 pg or 30,000 cpm of the radioiodinated derivative of the present invention is added to the diluted patient sample in the antibody coated tube. The reaction mixture is shaken briefly and allowed to incubate at 37° C. for 45 minutes. Competition between the unlabeled drug in the patient serum and the labeled derivative for the limited number of antibody binding sites available on the side of the tube determine the amount of antibody bound tracer, when the binding reaction is terminated. Separation of antibody bound and free tracer is effected by aspirating or decanting the aqueous phase that contains the free tracer. The tube containing the immobilized antibody bound tracer is counted in a gamma counter.

The compounds of the present invention allow the detection and quantitation of serum levels of 5,5-diphenylhydantoin with greater sensitivity and ease than had been possible previously with tritiated or carbon-14 labeled tracers, which suffer from relatively low specific activity and the necessity for the more laborious and cumbersome scintillation counting relative to gamma counting.

What is claimed is:
1. Radioiodinated 5,5-diphenylhydantoin-3-(5-valeryl-N-tyrosine).

* * * * *